(12) United States Patent
Favero et al.

(10) Patent No.: US 11,180,446 B2
(45) Date of Patent: Nov. 23, 2021

(54) ENHANCED OIL RECOVERY METHOD USING A (CO)POLYMER OF A HYDRATED CRYSTALLINE FORM OF 2-ACRYLAMIDO-2-METHYLPROPANE SULFONIC ACID

(71) Applicant: S.P.C.M. SA, Andrezieux Boutheon (FR)

(72) Inventors: Cédrick Favero, Andrezieux Boutheon (FR); Johann Kieffer, Andrezieux Boutheon (FR); Frédéric Daguerre, Andrezieux Boutheon (FR)

(73) Assignee: S.P.C.M. SA, Andrezieux Boutheon (FR)

(*) Notice: Subject to any disclaimer, the term of this patent is extended or adjusted under 35 U.S.C. 154(b) by 139 days.

(21) Appl. No.: 16/494,844

(22) PCT Filed: Mar. 19, 2018

(86) PCT No.: PCT/FR2018/050659
§ 371 (c)(1),
(2) Date: Sep. 17, 2019

(87) PCT Pub. No.: WO2018/172682
PCT Pub. Date: Sep. 27, 2018

(65) Prior Publication Data
US 2020/0079992 A1    Mar. 12, 2020

(30) Foreign Application Priority Data
Mar. 20, 2017  (FR) ...................................... 1752288

(51) Int. Cl.
*E21B 43/16* (2006.01)
*C07C 309/15* (2006.01)
(Continued)

(52) U.S. Cl.
CPC .............. *C07C 309/15* (2013.01); *C02F 1/56* (2013.01); *C02F 11/147* (2019.01); *C08F 20/58* (2013.01);
(Continued)

(58) Field of Classification Search
CPC .......... C09K 8/588; E21B 43/16; E21B 43/26
(Continued)

(56) References Cited

U.S. PATENT DOCUMENTS

| 10,759,746 B2 | 9/2020 | Favero et al. | |
| 2009/0099306 A1* | 4/2009 | Pich | B01F 3/1228 |
| | | | 524/827 |

(Continued)

FOREIGN PATENT DOCUMENTS

| FR | 2940348 A1 | 6/2010 |
| WO | 2010/133258 A1 | 11/2010 |
| WO | 2018/020175 A1 | 2/2018 |

OTHER PUBLICATIONS

Favero et al., "Hydrated Crystalline Form of 2-Acrylamido-2-Methylpropane Sulfonic Acid," U.S. Appl. No. 16/926,159, filed Jul. 10, 2020, 58 pp.
(Continued)

*Primary Examiner* — Zakiya W Bates
*Assistant Examiner* — Ashish K Varma
(74) *Attorney, Agent, or Firm* — Heslin Rothenberg Farley & Mesiti P.C.

(57) ABSTRACT

A process for enhanced oil recovery comprising the following steps:
a) Preparation of an injection fluid comprising at least one water-soluble (co)polymer prepared at least from 2-acrylamido-2-methylpropane sulfonic acid (ATBS) or from at least one of its salts, with water or with brine, where the 2-acrylamido-2-methylpropane sulfonic acid is a hydrated (Continued)

| Peak | Degree 2 theta | Peak | Degree 2 theta |
|---|---|---|---|
| 1 | 11,43 | 13 | 29,06 |
| 2 | 12,97 | 14 | 31,05 |
| 3 | 15,26 | 15 | 32,46 |
| 4 | 19,19 | 16 | 33,83 |
| 5 | 19,61 | 17 | 34,41 |
| 6 | 21,86 | 18 | 34,96 |
| 7 | 22,56 | 19 | 35,50 |
| 8 | 23,06 | 20 | 37,51 |
| 9 | 23,80 | 21 | 38,58 |
| 10 | 24,52 | 22 | 39,73 |
| 11 | 26,16 | 23 | 44,08 |
| 12 | 27,24 | 24 | 46,61 | crystalline form of 2-acrylamido-2-methylpropane sulfonic acid having a 2-theta powder X-ray diffraction diagram comprising peaks at 10.58°, 11.2°, 12.65°, 13.66°, 16.28°, 18.45°, 20°, 20.4°, 22.5°, 25.5°, 25.88°, 26.47°, 28.52°, 30.28°, 30.8°, 34.09°, 38.19°, 40.69°, 41.82°, 43.74°, 46.04° degrees.
b) Injection of injection fluid into an underground formation,
c) Flushing of the underground formation using the fluid injected,
d) Recovery of an aqueous and hydrocarbon mixture.

20 Claims, 10 Drawing Sheets

(51) Int. Cl.
| | | |
|---|---|---|
| C08F 20/58 | (2006.01) | |
| C09K 8/68 | (2006.01) | |
| C09K 8/80 | (2006.01) | |
| E21B 43/26 | (2006.01) | |
| C09K 8/588 | (2006.01) | |
| C02F 11/147 | (2019.01) | |
| C02F 1/56 | (2006.01) | |
| C02F 103/10 | (2006.01) | |

(52) U.S. Cl.
CPC ............... *C09K 8/588* (2013.01); *C09K 8/68* (2013.01); *C09K 8/80* (2013.01); *E21B 43/16* (2013.01); *E21B 43/26* (2013.01); *C02F 2103/10* (2013.01); *C07B 2200/13* (2013.01); *C09K 2208/28* (2013.01)

(58) Field of Classification Search
USPC ..................................................... 166/305.1
See application file for complete search history.

(56) References Cited

U.S. PATENT DOCUMENTS

| | | | | |
|---|---|---|---|---|
| 2010/0274048 | A1* | 10/2010 | Wakayama | ........... C07C 303/02 |
| | | | | 562/105 |
| 2014/0326457 | A1* | 11/2014 | Favero | ................. C08F 220/56 |
| | | | | 166/305.1 |
| 2019/0345373 | A1* | 11/2019 | Favero | ..................... C09K 8/64 |
| 2020/0048535 | A1 | 2/2020 | Favero et al. | |
| 2020/0087186 | A1* | 3/2020 | Favero | ..................... C09K 8/88 |

OTHER PUBLICATIONS

International Search Report (and English translation) and Written Opinion of the International Searching Authority for International Application No. PCT/FR2018/050659 dated Jun. 1, 2018.
Thomas, S., "Enhanced Oil Recovery—An Overview", Oil & Gas Science and Technology—Rev. IFP, vol. 63, No. 1, pp. 9-19 (2008).

* cited by examiner

ENHANCED OIL RECOVERY METHOD USING A (CO)POLYMER OF A HYDRATED CRYSTALLINE FORM OF 2-ACRYLAMIDO-2-METHYLPROPANE SULFONIC ACID

CROSS REFERENCE TO RELATED APPLICATIONS

This application is a national stage filing under section 371 of International Application No. PCT/FR2018/050659 filed on Mar. 19, 2018, and published on Sep. 27, 2018 as WO 2018/172682, which claims priority to French Application No. 1752288, filed on Mar. 20, 2017. The entire contents of WO 2018/172682 are hereby incorporated herein by reference.

FIELD OF THE INVENTION

The present invention relates to a process for enhanced oil and gas recovery using water-soluble (co)polymers made from the hydrated crystalline form of 2-acrylamido-2-methylpropane sulfonic acid (ATBS) or of at least one of its salts.

DESCRIPTION OF THE PRIOR ART

Most of the oil fields exploited currently have become mature and have therefore started to decline in production or are about to. The recovery level for these fields is currently of the order of 15 to 35% on average relative to the initial quantity of oil. Therefore, they offer even more considerable production potential.

Generally, crude oil contained in deposits is recovered in several stages.

The production results first from the natural energy of the fluids and rock that decompress. After this depletion phase, the quantity of oil recovered at the surface represents on average about 5 to 15% of the initial reserve. It is therefore necessary, in a second stage, to employ techniques targeting increased recovery yields while maintaining the pressure in the field.

The most frequent method consists of injecting water into the deposit through injection wells dedicated to this purpose. This is called secondary recovery. This second phase stops when the water/oil ratio is too high, i.e. when the quantity of water in the mixture produced by producing well is too high. This secondary recovery level produces additional recovery of the order of 10 to 20%.

The other techniques that can be used are together called enhanced oil recovery (EOR). Their goal is to recover between 10 and 35% of additional oil relative to the initial oil quantity. Diverse treatments with or without heat are known under the term enhanced oil recovery, such as techniques called electric, miscible, vapor, or chemical for improved recovery of remaining oil (See "Oil & Gas Science and Technology"—IFP review, vol 63 (2008) No. 1, pp 9-19).

"Oil" means any type of oil, i.e. both light and heavy oil, or even bitumen. An oil generally results from the natural transformation of organic material and is composed of a mixture of hydrocarbons. In the description of the prior art or of the invention, the terms "petroleum" and "oil" are used to denote the same material, with the exception of statements about the composition of an emulsion or dispersion.

The efficacy of flushing by water injection is generally improved through the addition of water-soluble (co)polymers. The expected and proven benefits of using the (co) polymer, through the "viscosification" of injected waters, are improved flushing and reduced viscosity contrast between the fluids, to control their mobility ratio in the field, so as to recover the oil quickly and effectively. These (co)polymers increase the water's viscosity.

It is known to the person skilled in the art that the synthetic water-soluble (co)polymers, particularly (co)polymers containing ATBS, are very advantageous (co)polymers for increasing the viscosity of aqueous solutions and are used in enhanced recovery. Indeed, (co)polymers containing ATBS are known to be tolerant to divalent salts and to high temperatures.

As well as increasing the viscosity of the water, the polymers used must have good filterability. (Co)polymers that have poor filterability tend to block the formation and slow or inhibit oil production. Filterability deteriorates when the molecular weight of the (co)polymer increases. Therefore, there is a delicate balance between molecular weight and filterability.

The (co)polymers added to injection water are generally subject to long rest times in the deposit, between the injection wells and the producing wells, which can range from a few months to a few years. During this period, they may undergo thermal degradation, leading to increased hydrolysis through the conversion of acrylamide or ATBS units into acrylates, or chemical degradation by free-radical attack, breaking the chain (lower molecular weight). In both cases, these mechanisms generally translate to reduced viscosity and therefore to less effective oil flushing by the aqueous solution of polymer injected into the reservoir. Therefore, there is a real interest in developing polymers that are stronger for these processes involved in any enhanced oil or gas recovery project.

The present invention relates to providing water-soluble polymers that present improved properties in particular in terms of filterability and improved chemical and thermal stability, particularly useful in enhanced oil and gas recovery techniques.

DISCLOSURE OF THE INVENTION

The invention relates to the use of a new hydrated crystalline form of 2-acrylamido-2-methylpropane sulfonic acid for preparing water-soluble (co)polymers.

"Water-soluble (co)polymer" denotes a (co)polymer that can be solubilized in water or brine in the conventional conditions encountered in enhanced oil or gas recovery processes, generally between 10 ppm and 15,000 ppm by weight as indicated below.

Secondly, and unless otherwise indicated, "2-acrylamido-2-methylpropane sulfonic acid in hydrated crystalline form" denotes the acid form and/or the salified form. The same is the case for the anionic monomers mentioned below that may denote the acid and/or salified forms like, for example, for acrylic acid.

The salt form is advantageously obtained from a compound chosen from among an alkali or alkaline earth metal hydroxide, an alkali or alkaline metal earth oxide, ammonia, an amine having the following formula $NR_1R_2R_3$ ($R_1$, $R_2$ and $R_3$ being advantageously hydrocarbon groups, in particular alkyl groups) or an alkali or alkaline earth metal carbonate. A preferred alkaline metal is sodium.

The acid form of a monomer can be salified before and/or during and/or after the (co)polymerization of the monomer or monomers.

Another feature of the invention relates to an enhanced oil recovery process characterized in that it comprises the following steps:
a) Preparation of an injection fluid comprising at least one water-soluble (co)polymer made from the hydrated crystalline form of 2-acrylamido-2-methylpropane sulfonic acid or from at least one of its salts, with water or with brine,
b) Injection of injection fluid into an underground formation,
c) Flushing the underground formation using the fluid injected,
d) Recovery of an aqueous and hydrocarbon mixture.

The hydrated crystalline form of 2-acrylamido-2-methylpropane sulfonic acid has a 2-theta powder X-ray diffraction diagram comprising peaks at 10.58°, 11.2°, 12.65°, 13.66°, 16.28°, 18.45°, 20°, 20.4°, 22.5°, 25.5°, 25.88°, 26.47°, 28.52°, 30.28°, 30.8°, 34.09°, 38.19°, 40.69°, 41.82°, 43.74°, 46.04° degrees. The uncertainty in these peaks is generally of the order of 0.1°.

X-ray crystallography, radiocrystallography or X-ray diffractometry is an analytical technique for studying the structure of the crystalline material on the atomic scale. It uses the physical phenomenon of X-ray diffraction. A diffractometer having a copper source may be used.

A powder formed from a specific crystalline phase will always produce diffraction peaks in the same directions. So this diffraction diagram forms a real signature of the crystalline phase. It is therefore possible to determine the nature of each crystalline phase within a mixture or a pure product.

This signature is specific to each crystalline organic or inorganic compound, and presents in the form of a list of peaks with positions at the 2θ angle (2-theta).

This technique is used to characterize the material, particularly the different crystalline forms that may exist for a given chemical molecule.

The hydrated crystalline form of 2-acrylamido-2-methylpropane sulfonic acid has a Fourier transform infrared spectrum comprising peaks at 3280 $cm^{-1}$, 3126 $cm^{-1}$, 1657 $cm^{-1}$, 1595 $cm^{-1}$, 1453 $cm^{-1}$, 1395 $cm^{-1}$, 1307 $cm^{-1}$, 1205 $cm^{-1}$, 1164 $cm^{-1}$, 1113 $cm^{-1}$, 1041 $cm^{-1}$, 968 $cm^{-1}$, 885 $cm^{-1}$, 815 $cm^{-1}$, 794 $cm^{-1}$. The uncertainty in these peaks is generally of the order of 8 $cm^{-1}$. Advantageously, this is the solid spectrum obtained conventionally in a salt such as KBr.

Fourier transform infrared spectroscopy is the analysis of vibrations emitted, absorbed or diffused by the molecules. This technique is sensitive to close interactions (influence of the lattice unit on the bonds). In the majority of cases, the Fourier transform infrared spectra for different crystalline systems differ significantly. So the Fourier transform infrared spectrum reflects details about the crystalline structure of an organic compound.

Generally, and unless otherwise indicated, the X-ray diffraction diagram and the infrared spectrum are obtained at 20° C. and atmospheric pressure of 1 atmosphere (101,325 Pa).

The hydrated crystalline form of 2-acrylamido-2-methylpropane sulfonic acid has minimum ignition energy greater than 400 mJ, preferably greater than 500 mJ (1 mJ=$10^{-3}$ Joule).

The minimum ignition energy represents the minimum energy that must be provided to a compound to cause ignition. The energy may be electric or thermal. The minimum ignition energy is an essential piece of data for taking into account the risk of explosion during product handling (transfer, storage, reaction, shaping, etc.).

The minimum ignition energy depends on the powder's properties (composition) and its macromolecular structure (particle size, crystalline form, specific surface area).

For solids, this energy is the minimum energy of an electrical spark that can ignite a cloud of dust. The higher the minimum ignition energy, the lower the risk the solid presents during use, handling, storage.

Minimum ignition energy was measured according to standard NF EN 13821.

The hydrated crystalline form of 2-acrylamido-2-methylpropane sulfonic acid presents 4 thermal phenomena with the differential scanning calorimetry technique, at 70° C., 100° C., 150° C. and 190° C. The relative uncertainty when observing these phenomena is generally of the order of 10° C., advantageously 5° C. or less.

The thermal phenomena are measured by differential scanning calorimetry (DSC). This technique measures the heat variation associated with thermal denaturation of the compound when it is heated at a constant rate, for example with a heating ramp of 10° C./minute.

It is generally recognized that the thermal phenomenon that occurs at 190° C. (+/−10° C.) is related to the melting point of 2-acrylamido-2-methylpropane sulfonic acid.

The invention relates to the use of a new hydrated crystalline form of 2-acrylamido-2-methylpropane sulfonic acid or of at least one of its salts for preparing water-soluble (co)polymers.

According to a specific embodiment of the invention, the water-soluble (co)polymer is obtained at least from 2-acrylamido-2-methylpropane sulfonic acid of which 50% to 100% is in the hydrated crystalline form, more advantageously 70 to 100%, and even more advantageously 100%.

The water-soluble (co)polymer is advantageously obtained from between 1 and 100 mol % of 2-acrylamido-2-methylpropane sulfonic acid, preferably between 5 and 100 mol % of 2-acrylamido-2-methylpropane sulfonic acid, even more preferably between 25 and 100 mol % of 2-acrylamido-2-methylpropane sulfonic acid; 50% to 100% of 2-acrylamido-2-methylpropane sulfonic acid being advantageously in the hydrated crystalline form, more advantageously 70 to 100%, and even more advantageously 100%.

Generally, the person skilled in the art will know, if need be, how to adjust the quantity of any additional monomers (anionic and/or cationic and/or zwitterionic) listed below to reach 100 mol %.

According to a specific embodiment of the invention, the water-soluble (co)polymer is obtained from 2-acrylamido-2-methylpropane sulfonic acid of which 50% to 100% is advantageously in the hydrated crystalline form (more advantageously 70 to 100%, and even more advantageously 100%) and of at least one nonionic monomer; and/or at least one anionic monomer and/or at least one cationic monomer and/or a zwitterionic monomer.

The nonionic monomer or monomers that can be used in the scope of the invention can be chosen, in particular, in the group comprising water-soluble vinyl monomers. Preferred monomers belonging to this class are, for example, acrylamide, methacrylamide, N-isopropylacrylamide, N,N-dimethylacrylamide, N,N-diethylacrylamide and N-methylolacrylamide. The following may also be used: N-vinylformamide, N-vinyl acetamide, N-vinylpyridine and N-vinylpyrrolidone, N-vinyl imidazole, N-vinyl succinimide, acryloyl morpholine (ACMO), acryloyl chloride, glycidyl methacrylate, glyceryl methacrylate, diacetone acrylamide and isoprenol. A preferred nonionic monomer is acrylamide.

According to a particular embodiment, the (co)polymer is advantageously obtained from between 1 and 99.9 mol % of nonionic monomer(s), preferably between 40 and 95 mol % and more preferably between 45 and 90 mol %, relative to the total number of monomers. In this case, the (co)polymer is advantageously obtained from between 0.1 and 99 mol % of 2-acrylamido-2-methylpropane sulfonic acid; 50% to 100% of 2-acrylamido-2-methylpropane sulfonic acid being advantageously in the hydrated crystalline form, more advantageously 70 to 100%, and even more advantageously 100%.

The anionic monomer(s) that may be used within the scope of the invention may be selected from a wide group. These monomers may have acrylic, vinyl, maleic, fumaric, malonic, itaconic, allylic functional groups and contain a carboxylate, phosphonate, phosphate, sulfate, sulfonate group or another anionic group. The anionic monomer may be in acid form or in the form of an alkaline earth metal salt, an alkali metal salt or an ammonium salt. Examples of monomers include acrylic acid, methacrylic acid, itaconic acid, crotonic acid, maleic acid, fumaric acid, acrylamido undecanoic acid, 3-acrylamido 3-methylbutanoic acid, maleic anhydride; monomers of the strong acid type having for example a function of the sulfonic acid or phosphoric acid type, such as vinylsulfonic acid, vinylphosphonic acid, allylsulfonic acid, methallylsulfonic acid, 2-methylidenepropane-1,3-disulfonic acid, 2-sulfoethylmethacrylate, sulfopropylmethacrylate, sulfopropylacrylate, allylphosphonic acid, styrene sulfonic acid, 2-acrylamido-2-methyl propane disulfonic acid; and water-soluble salts of these monomers like their alkali metal, alkaline earth metal, or ammonium salts. In this list, the strong acid monomers mentioned having a sulfonic acid function do not include the hydrated crystalline form of 2-acrylamido-2-methylpropane sulfonic acid.

According to a particular embodiment, the copolymer is advantageously obtained from between 1 and 99 mol % of anionic monomer(s), preferably between 5 and 60 mol % and more preferably between 10 and 50 mol %, relative to the total number of monomers. In this case, these percentages also include the hydrated crystalline form of 2-acrylamido-2-methylpropane sulfonic acid according to the invention.

The cationic monomer or monomers that can be used in the scope of the invention may be chosen from among monomers derived from units of the acrylamide, acrylic, vinyl, allyl or maleic type, where these monomers have a quaternary phosphonium or ammonium function. Mention may be made, in particular and in a non-limiting way, of quaternized dimethylaminoethyl acrylate, quaternized dimethylaminoethyl acrylate, dimethyldiallylammonium chloride (DADMAC), acrylamido propyltrimethyl ammonium chloride (APTAC) and methacrylamido propyltrimethyl ammonium chloride (MAPTAC). The quaternization agent may be chosen from alkyl chlorides, dialkyl sulfates or alkyl halides. Preferably, the quaternization agent is chosen from methyl chloride or diethyl sulfate.

The zwitterionic monomer may be a derivative of a unit of the acrylamide, acrylic, vinyl, allyl or maleic type having an amine or quaternary ammonium function and an acid function like a carboxylic (or carboxylate), sulfonic (or sulfonate) or phosphoric (or phosphate). Mention may be made, specifically and in a non-limiting manner, of dimethylaminoethyl acrylate derivatives, such as 2-((2-(acryloyloxy)ethyl) dimethylammonio) ethane-1-sulfonate, 3-((2-(acryloyloxy)ethyl) dimethylammonio) propane-1-sulfonate, 4-((2-(acryloyloxy)ethyl) dimethylammonio) butane-1-sulfonate, [2-(acryloyloxy)ethyl] (dimethylammonio) acetate, dimethylaminoethyl methacrylate derivatives such as 2-((2-(methacryloyloxy) ethyl) dimethylammonio) ethane-1-sulfonate, 3-((2-(methacryloyloxy) ethyl) dimethylammonio) propane-1-sulfonate, 4-((2-(methacryloyloxy) ethyl) dimethylammonio) butane-1-sulfonate, [2-(methacryloyloxy)ethyl)] (dimethylammonio) acetate, dimethylamino propylacrylamide derivatives such as 2-((3-acrylamidopropyl) dimethylammonio) ethane-1-sulfonate, 3-((3-acrylamidopropyl) dimethylammonio) propane-1-sulfonate, 4-((3-acrylamidopropyl) dimethylammonio) butane-1-sulfonate, [3-(acryloyloxy) propyl)] (dimethylammonio) acetate, dimethylamino propyl methylacrylamide derivatives such as 2-((3-methacrylamidopropyl) dimethylammonio) ethane-1-sulfonate, 3-((3-methacrylamidopropyl) dimethylammonio) propane-1-sulfonate, 4-((3-methacrylamidopropyl) dimethylammonio) butane-1-sulfonate and [3-(methacryloyloxy)propyl] (dimethylammonio) acetate.

Monomers with hydrophobic character may also be used in the invention. They are preferably selected from the group consisting of (meth)acrylic acid esters having an alkyl, arylalkyl, propoxylated, ethoxylated, or propoxylated and ethoxylated, or dialkyl chain; alkyl aryl sulfonates.

When a monomer having a hydrophobic nature is used, its quantity lies advantageously within the range between 0.001 and 3 mol % relative to the total quantity of monomers.

Monomers with a fluorescent function may also be used in the scope of the invention. A monomer with a fluorescent function may be detected by any appropriate method, for example by fluorimetry with a fixed wavelength fluorimeter. Generally, the monomer having a fluorescent function is detected at the excitation and emission maxima, which can be determined using a scanning fluorimeter.

Monomers having a fluorescent function are chosen from, for example, monomers of the sodium sulfonate styrene or sulfonic styrene type.

The water-soluble (co)polymer is preferably an anionic (co)polymer containing acrylamide and 2-acrylamido-2-methylpropane sulfonic acid; 50% to 100% of 2-acrylamido-2-methylpropane sulfonic acid being in the hydrated crystalline form, optionally partially post-hydrolyzed, more preferably an acrylamide, acrylic acid and 2-acrylamido-2-methylpropane sulfonic acid terpolymer, or of at least one of their salts; 50% to 100% of 2-acrylamido-2-methylpropane sulfonic acid being in the hydrated crystalline form. In both cases, the (co)polymer can be partially or totally post hydrolyzed, the anionic monomers that can be in the acid or salified form.

The water-soluble (co)polymer is preferably obtained from between 10 mol % and 100 mol % of anionic monomer(s), more preferably between 20 mol % and 100 mol %, where these percentages include the monomer corresponding to the hydrated crystalline form of 2-acrylamido-2-methylpropane sulfonic acid or one of its salts.

The water-soluble (co)polymer is preferably obtained from between 10 mol % and 100 mol % of the hydrated crystalline form of 2-acrylamido-2-methylpropane sulfonic acid.

In a preferred manner, the water-soluble (co)polymer contains only monomeric anionic and nonionic units. In other words, it is preferably obtained from at least one anionic monomer and at least one nonionic monomer.

According to the invention, the water-soluble (co)polymer used may have a linear, branched, star-shaped, comb-shaped or block structure. These structures may be obtained by the selection of the initiator, transfer agent, polymerization technique, such as controlled radical polymerization known as RAFT (reversible-addition fragmentation chain transfer), NMP (nitroxide-mediated polymerization) or ATRP (atom-transfer radical polymerization), incorporation of structural monomers, or concentration, etc.

Generally, the (co)polymer does not require the development of any particular polymerization method. Indeed, it may be obtained according to polymerization techniques known by a person skilled in the art. It may notably be solution polymerization, gel polymerization, precipitation polymerization, emulsion polymerization (aqueous or inverse), suspension polymerization, reactive extrusion polymerization, or micellar polymerization.

According to a specific embodiment of the invention, the (co)polymer may be post-hydrolyzed. Post-hydrolysis is the reaction of the (co)polymer after polymerization. This step consists in reacting the hydrolyzable functional groups on the advantageously nonionic monomers, more advantageously amide or ester functions, with a hydrolysis agent. This hydrolysis agent may be an enzyme, an ion exchange resin, or an alkali metal. Preferably, the hydrolysis agent is a base. During this copolymer post-hydrolysis step, the number of carboxylic acid functions increases. The reaction between the base and the amide or ester functions in the copolymer product produces carboxylate groups.

According to the invention, the (co)polymer may be in the form of a liquid, gel or solid when its preparation includes a drying step such as spray drying, tumble drying, drying by electromagnetic radiation such as microwave or fluidized bed drying.

According to the invention, the water-soluble (co)polymer is linear or structured. Structured (co)polymer denotes a non-linear (co)polymer that has side chains so as to obtain, when this (co)polymer is dissolved in water, a high state of tangling leading to viscosities with very high low gradients. The water-soluble (co)polymer according to the invention is not generally crosslinked.

The water-soluble (co)polymer may in addition be structured:
  by at least one structure agent, which can be chosen from the group comprising unsaturated polyethylene monomers (having at least two unsaturated functions), such as for example vinyl, allyl, acrylic and epoxy functions and for example mention may be made of methylene-bis-acrylamide (MBA), triallyamine, tetraallylammonium chloride, or 1,2-dihydroxyethylene bis-(N-acrylamide), and/or
  by macroinitiators such as polyperoxides, polyazoics and poly transfer agents such as polymercaptan (co)polymers, and polyols, and/or
  by functionalized polysaccharides.

The quantity of branching/crosslinking agent in the monomer mixture is advantageously less than 4% by weight relative to the monomer content, more advantageously less than 1% and even more advantageously less than 0.5%. According to a specific embodiment, it may at least equal to 0.00001% by weight relative to the monomer content.

According to a specific embodiment, the water-soluble (co)polymer may comprise at least one LCST group.

According to the general knowledge of a person skilled in the art, LCST groups correspond to groups whose water solubility for a determined concentration is modified beyond a certain temperature and as a function of the salinity. This is a group having a heating transition temperature defining its lack of affinity with the solvent medium. The lack of affinity with the solvent results in opacification or loss of transparency, which may be due to precipitation, aggregation, gelification, or viscosification of the medium. The minimum transition temperature is known as "LCST" (Lower Critical Solution Temperature). For each concentration of the LCST group, a heating transition temperature is observed. It is greater than the LCST, which is the minimum point in the curve. Below this temperature, the polymer is soluble in water; above this temperature, the polymer loses its solubility in water.

According to a specific embodiment, the water-soluble (co)polymer may comprise at least one UCST group.

According to the general knowledge of a person skilled in the art, UCST groups correspond to groups whose water solubility for a determined concentration is modified beyond a certain temperature and as function of the salinity. This is a group having a cooling transition temperature defining its lack of affinity with the solvent medium. The lack of affinity with the solvent results in opacification or loss of transparency, which may be due to precipitation, aggregation, gelification, or viscosification of the medium. The maximum transition temperature is known as "UCST" (Upper Critical Solution Temperature). For each concentration of the UCST group, a cooling transition temperature is observed. It is lower than the UCST, which is the maximum point in the curve. Above this temperature, the (co)polymer is soluble in water; below this temperature, the (co)polymer loses its water solubility.

According to the invention, the (co)polymer has an advantageously high molecular weight. "High molecular weight" denotes molecular weights of at least 1 million g/mol, preferably between 2 and 40 million g/mol, more preferably between 5 and 30 million g/mol. Molecular weight is understood as average molecular weight by weight.

According to the invention, the (co)polymer has a filter ratio (FR, or filtration quotient) less than 1.5, preferably less than 1.3, more preferably less than 1.1.

The term filter ratio is used in this document to denote a test used to determine the performance of the polymer solution in conditions that approach the deposit's permeability consisting of measuring the time taken by given solution volumes/concentrations to cross a filter. The FR generally compares the filterability of the polymer solution for two equivalent consecutive volumes, which indicates the tendency of the solution to block the filter. The lowest FR indicate a better yield.

The test used to determine the FR consists of measuring the time that the given volumes of solution with 1000 ppm of polymer active take to flow through a filter. The solution is contained in a pressurized cell at two bars of pressure and the filter is 47 mm in diameter and has a defined pore size. Generally the FR is measured with filters having a pore size of 1.2 µm, 3 µm, 5 µm or 10 µm.

The necessary times to obtain 100 mL ($t_{100\ mL}$); 200 mL ($t_{200\ mL}$) and 300 mL ($t_{300\ mL}$) of filtrate are therefore measured and a FR is defined, expressed by:

$$FR = \frac{t_{300ml} - t_{200ml}}{t_{200ml} - t_{100ml}}$$

The times are measured to the nearest 0.1 second.

So the FR represents the capacity of the polymer solution to block the filter for two consecutive, equivalent volumes.

The (co)polymers used according to the invention have improved resistance to chemical degradation and thermal degradation relative to (co)polymers with equivalent molecular weights made from 2-acrylamido-2-methylpropane sulfonic acid that is not in the hydrated crystalline form.

The test used to determine the resistance to chemical degradation consists in preparing a polymer solution at a given concentration in a given brine in aerobic conditions and putting it in contact with a chemical contaminant such as iron or hydrogen sulfide. The viscosity of the polymer solution is measured before and after 24 h of exposure to the contaminant. The viscosity measurements are made under the same temperature and shear gradient conditions.

The test used to determine the resistance to mechanical degradation consists of preparing a polymer solution at a given concentration in a brine with a given composition under anaerobic conditions (use of a glove box purged with nitrogen) and leaving it in a stainless-steel cell placed at a given temperature for a predefined period. At the end, the stainless-steel cell is cooled to ambient temperature, then the viscosity of the polymer solution that it contains is measured and compared to its initial value. Any manipulation of the stainless-steel cell is done in the glove box to prevent any exposure to oxygen. The stainless-steel cells are airtight to prevent any oxygen entry into the solution during aging at temperature. The viscosity measurements before and after aging are made under the same temperature and rate gradient conditions.

Resistance to chemical degradation and thermal degradation are quantified by the loss of viscosity expressed as a percentage and determined at the end by:

$$\text{Viscosity loss (\%)} = \frac{Viscosity_{initial} - Viscosity_{final}}{Viscosity_{initial}} \times 100$$

More precisely, the present invention also relates to a process for enhanced oil and/or gas recovery using at least one water-soluble (co)polymer made from the hydrated crystalline form of 2-acrylamido-2-methylpropane sulfonic acid or of at least one of its salts mentioned above (alkali metals salts, alkaline earth metal salts, or ammonium salts).

As already indicated, the invention relates to an enhanced oil recovery process, characterized in that it comprises the following steps:
 a) Preparation of an injection fluid comprising at least one water-soluble (co)polymer made at least from the hydrated crystalline form of 2-acrylamido-2-methylpropane sulfonic acid or from at least one of its salts, with water or with brine,
 b) Injection of injection fluid into an underground formation,
 c) Flushing of the underground formation using the fluid injected,
 d) Recovery of an aqueous and hydrocarbon mixture.

When the water-soluble (co)polymer is in the form of particles, it can be dissolved in an aqueous medium in a dispersion device. An example of a dispersion device is the polymer grinding unit (PSU) described in document U.S. Pat. No. 8,186,871, which can prepare a concentrated aqueous solution of polymer.

The water or brine used to prepare the injection fluid may be a production water. "Production water" is understood to mean all fresh or salt water, brines, sea water, aquifer water that come from a hydrocarbon reservoir. This production water can previously be treated before the preparation of the injection fluid as described in patent application WO 2018/020175.

The water-soluble (co)polymers may be combined with stabilizing compounds. The stabilizing compounds (stabilizers) may be compounds that suitably protect the (co)polymer, for example from thermal, chemical and/or mechanical degradation. Examples of appropriate stabilizers are provided in patent application WO 2010/133258, which is integrated by reference.

The injection of the injection fluid comprising the water-soluble (co)polymer, according to the technique employed, is done alone or in conjunction with one or more chemicals useful to enhanced oil recovery. Among these chemical compounds, the use of weak, strong or extra strong organic or inorganic bases can be cited, which can saponify the crudes and produce surfactant species in situ that solubilize the oil. As an example, among these are found sodium carbonate, sodium hydroxide, borate and metaborate compounds, amines, basic polymeric species. Another family of widely injected compounds with the polymers is that of surfactant compounds, often anionic, zwitterionic, cationic and sometimes also nonionic. These compounds are rarely injected pure but with a co-surfactant and a co-solvent to improve their compatibility and efficacy in the reservoir.

According to the invention, the injection fluid advantageously comprises between 10 ppm and 15,000 ppm of water-soluble (co)polymer, more advantageously between 50 and 10,000 ppm, and even more advantageously between 100 and 5,000 ppm.

In a totally surprising manner, the Applicant has discovered that the water-soluble (co)polymer made from the hydrated crystalline form of 2-acrylamido-2-methylpropane sulfonic acid or of at least one of its salts has better filterability and better resistance to chemical degradation and thermal degradation than (co)polymers with equivalent molecular weights made from 2-acrylamido-2-methylpropane sulfonic acid that are not in the hydrated crystalline form. The (co)polymers of the invention have improved filterability relative to (co)polymers with equivalent molecular weights made from 2-acrylamido-2-methylpropane sulfonic acid that is not in the hydrated crystalline form. Moreover, it is known that filterability deteriorates when the molecular weight of the (co)polymer increases. The interest of the invention is that (co)polymers with very high molecular weight may be obtained while having good filterability. What is more, the polymer concentration necessary to reach a target injection fluid viscosity is reduced, which improves the economic conditions of the recovery of the hydrocarbon and/or gas contained in the underground formation.

The water-soluble (co)polymers according to the invention have the functionality of viscosifying the waters injected into the reservoirs containing oil or gas to ensure mobility control without recourse to crosslinking, i.e. an inter-chain chemical bridge, being necessary.

According to a specific embodiment of the invention, the enhanced oil recovery process is characterized in that it comprises the following steps:
 a) Preparation of an injection fluid comprising (co)polymers having a molecular weight greater than 5 million, characterized in that
  the injection fluid has a salt concentration greater than 100 g/L, of which at most 50 g/L of divalent salt(s),
  the (co)polymers are obtained at least from at least 80 mol % of ATBS, where 50% to 100% is in hydrated crystalline form and/or at least one of its salts,
  the polymer concentration of the injection fluid is less than 3000 ppm by weight,
  the injection fluid before shear step b) has a viscosity $V_1$, b) Shear of the injection fluid to obtain a drop in viscosity of more than 25% relative to $V_1$ and characterized in that $$\frac{V2 - V_{water}}{V_{water}} \geq 3$$

where,
$V_2$ is the viscosity of the injection fluid after shear at the temperature of the formation.
$V_{water}$ is the viscosity of the water used to prepare the injection fluid at the temperature of the formation.
c) Injection of the injection fluid into an underground formation, characterized in that the underground formation is a carbonate formation having permeability less than 300 millidarcy and at temperature greater than 100° C.,
d) Flushing the underground formation using the fluid injected,
e) Recovery of an aqueous and hydrocarbon mixture.
V1 corresponds to the viscosity of the injection fluid before the shear step at the temperature of the formation.

As already indicated, V2 corresponds to the viscosity of the injection fluid after the shear step at the temperature of the formation. $V_{water}$ corresponds to the viscosity of the water used to prepare the injection fluid at the temperature of the formation.

The shear step may be conducted, for example, using a valve, an orifice or a pump.

Preferably, the divalent salt concentration in the injection fluid is inclusively between 3 and 50 g/L.

Carbonate formations are sedimentary rock formations whose carbonate composition is at least 50%.

The invention and the advantages resulting from it will be brought out more clearly by the following figures and examples given to illustrate the invention and without limitation.

EXAMPLE EMBODIMENTS OF THE INVENTION

Example 1: Synthesis of 2-acrylamido-2-methylpropane Sulfonic Acid

To a stirred 2000-mL jacketed reactor, 1522 grams of acrylonitrile was added containing 0.4% of water by weight and 180 grams of fuming sulfuric acid titrating at 104% $H_2SO_4$ (18% Oleum). The mixture was stirred for 1 hour and cooled via the reactor jacket, which held the temperature of the sulfonating mixture at −20° C.

To the previous sulfonating mixture, 97 grams of isobutylene was added, at a flow rate of 1.6 grams/minute.

The temperature of the mixture was controlled at 45° C. while isobutylene was added. The particles of 2-acrylamido-2-methylpropane sulfonic acid precipitate in the mixture and the solid content was about 20% by weight. The reaction mixture was filtered on a Buchner filter and dried under vacuum at 50° C. The solid obtained was 2-acrylamido-2-methylpropane sulfonic acid; it was present in the form of a very fine white powder.

Example 2: Synthesis of the Hydrated Crystalline Form of 2-acrylamido-2-methylpropane Sulfonic Acid To a 2000-mL jacketed reactor, 500 grams of 2-acrylamido-2-methylpropane sulfonic acid obtained in example 1 and 460 grams of sulfuric acid at a concentration of 10% $H_2SO_4$ were added.

250 mg of 4-hydroxy-2,2,6,6-tetramethylpiperidin-1-oxyl was added to the preceding mixture.

The mixture was stirred for 10 minutes, at 20° C., to form suspension A.

Suspension A was heated to a temperature of 60° C. and maintained at this temperature for 20 minutes to form solution B.

Solution B was cooled to a temperature of 10° C. The cooling time between 60° C. and 10° C. was 6 hours. Suspension C of crystals of 2-acrylamido-2-methylpropane sulfonic acid was obtained. Suspension C was filtered on a vertical Robatel centrifugal dryer. A solid of composition 1 was obtained, containing 80% by weight of 2-acrylamido-2-methylpropane sulfonic acid crystals.

Example 3: X-Ray Diffraction Analysis

The solids obtained in examples 1 and 2 were previously ground to form powders and were analyzed by X-ray diffraction over an angular range from 10 to 90°. The equipment used was a Rigaku miniflex II diffractometer equipped with a copper source.

Figure 1:
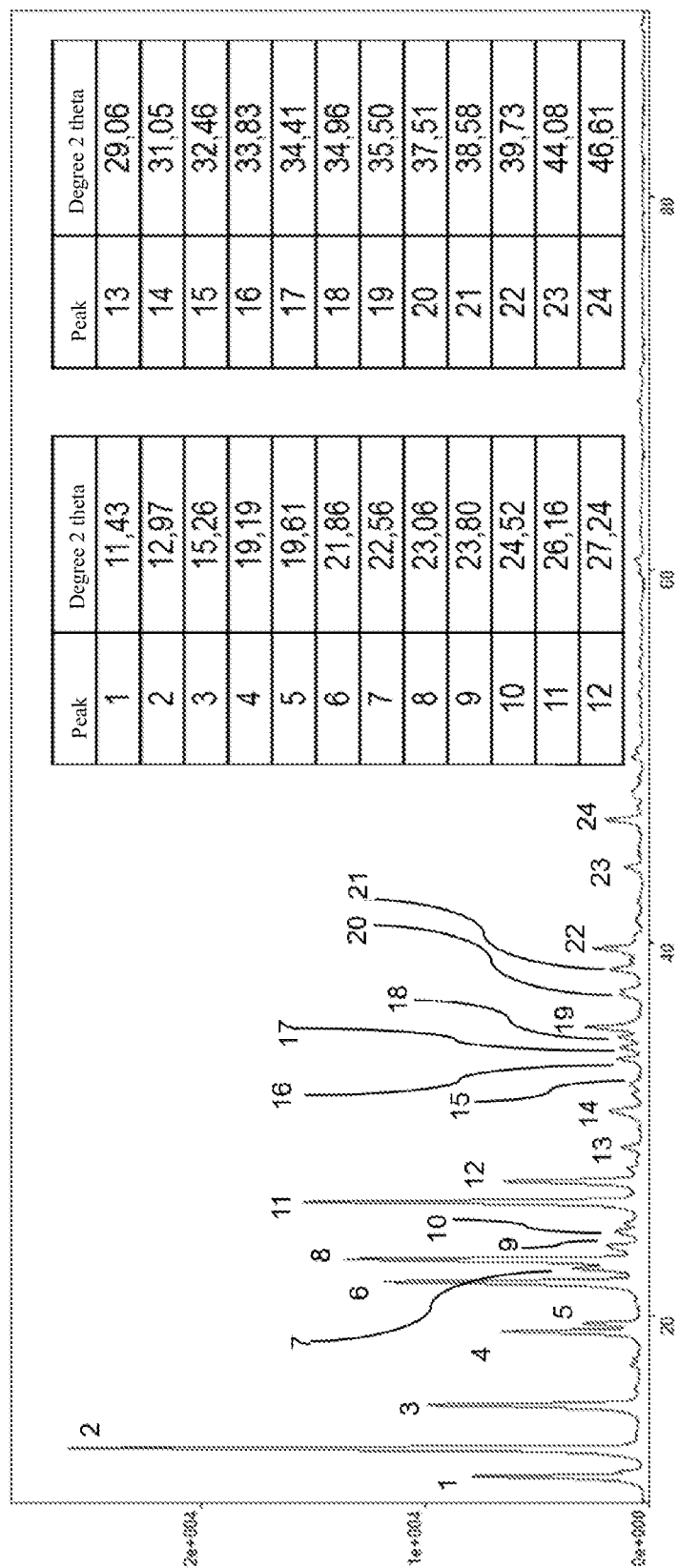
FIG. 1 illustrates the X-ray diffraction diagram of the crystals obtained according to example 1.
Figure 2:
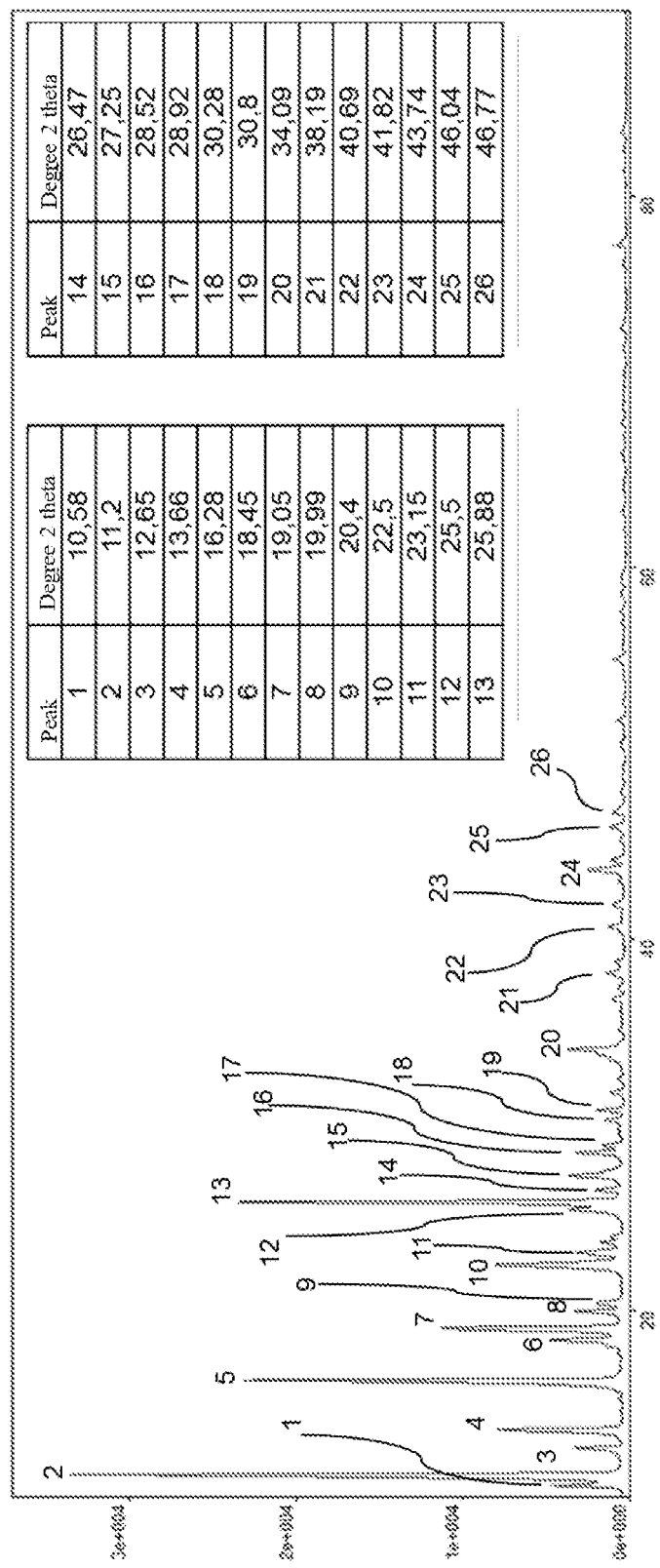
FIG. 2 illustrates the X-ray diffraction diagram of the crystals obtained according to example 2.

We observed that the solid obtained from example 2 (FIG. 2) has a 2-theta X-ray diffraction diagram with the following characteristic peaks:

10.58°, 11.2°, 12.65°, 13.66°, 16.28°, 18.45°, 20°, 20.4°, 22.5°, 25.5°, 25.88°, 26.47°, 28.52°, 30.28°, 30.8°, 34.09°, 38.19°, 40.69°, 41.82°, 43.74°, 46.04° 2-Theta degrees (+/−0.1°).

Example 4: Fourier Transform Infrared Measurement

The equipment for Fourier transform infrared measurement was the Perkin Elmer Spectrum 100, whose precision is 8 cm$^{-1}$.

The solids obtained in examples 1 and 2 were sieved at 100 μm. The particles remaining on the sieve were dried and put in the oven at 60° C. for at least 4 hours.

10 mg of solid was weighed precisely and mixed with 500 mg of potassium bromide (KBr). The mixture was then compacted in a hydraulic press under a pressure of at least 10 bars.

Figure 4:
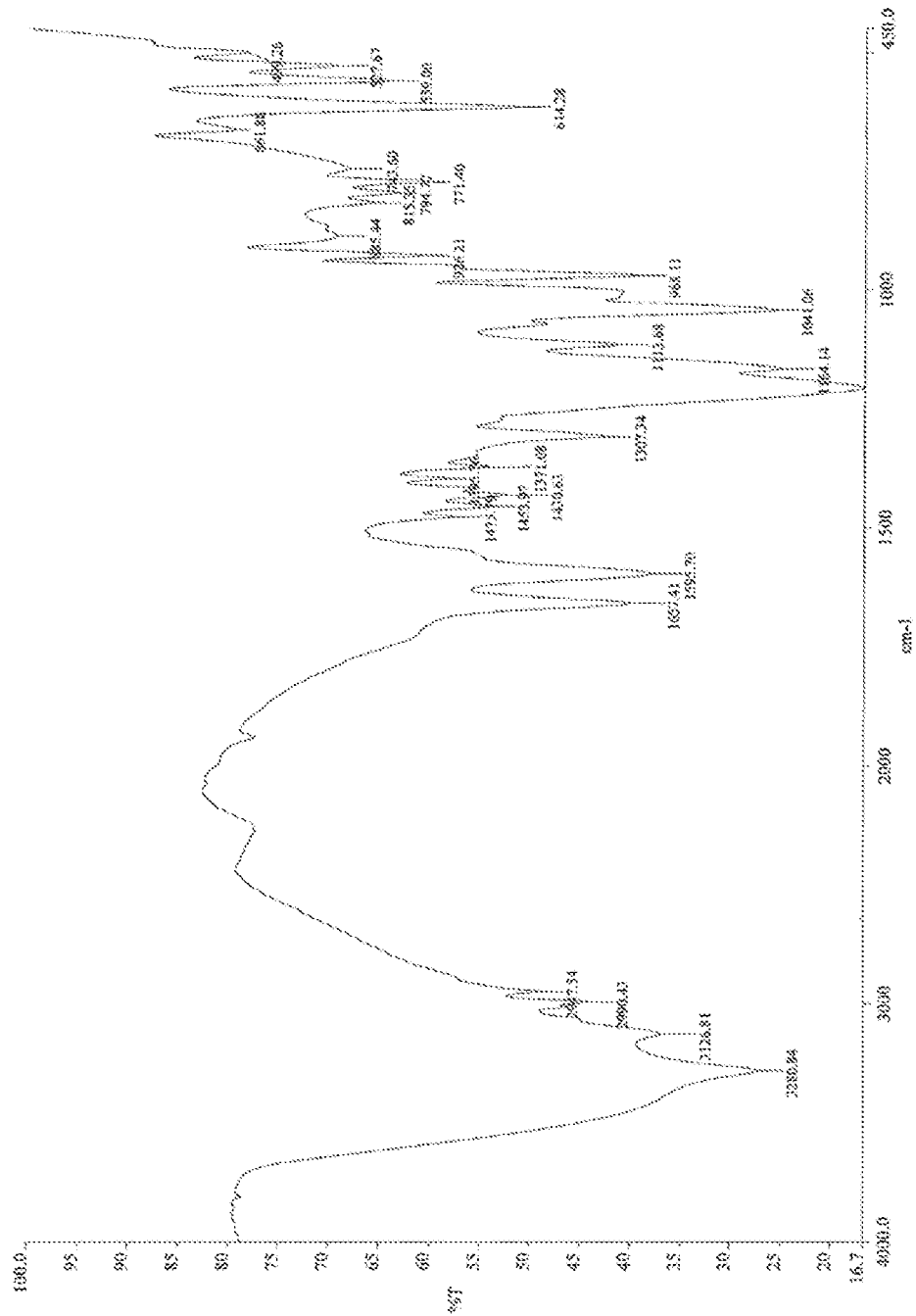
FIG. 4 illustrates the X-ray diffraction diagram of the crystals obtained according to example 2.

We observed that the following bands (FIG. 4) are characteristic of the hydrated crystalline form of 2-acrylamido-2-methylpropane sulfonic acid:

3280 cm$^{-1}$, 3126 cm$^{-1}$, 1657 cm$^{-1}$, 1595 cm$^{-1}$, 1453 cm$^{-1}$, 1395 cm$^{-1}$, 1307 cm$^{-1}$, 1205 cm$^{-1}$, 1164 cm$^{-1}$, 1113 cm$^{-1}$, 1041 cm$^{-1}$, 968 cm$^{-1}$, 885 cm$^{-1}$, 815 cm$^{-1}$, 794 cm$^{-1}$.

Figure 3:
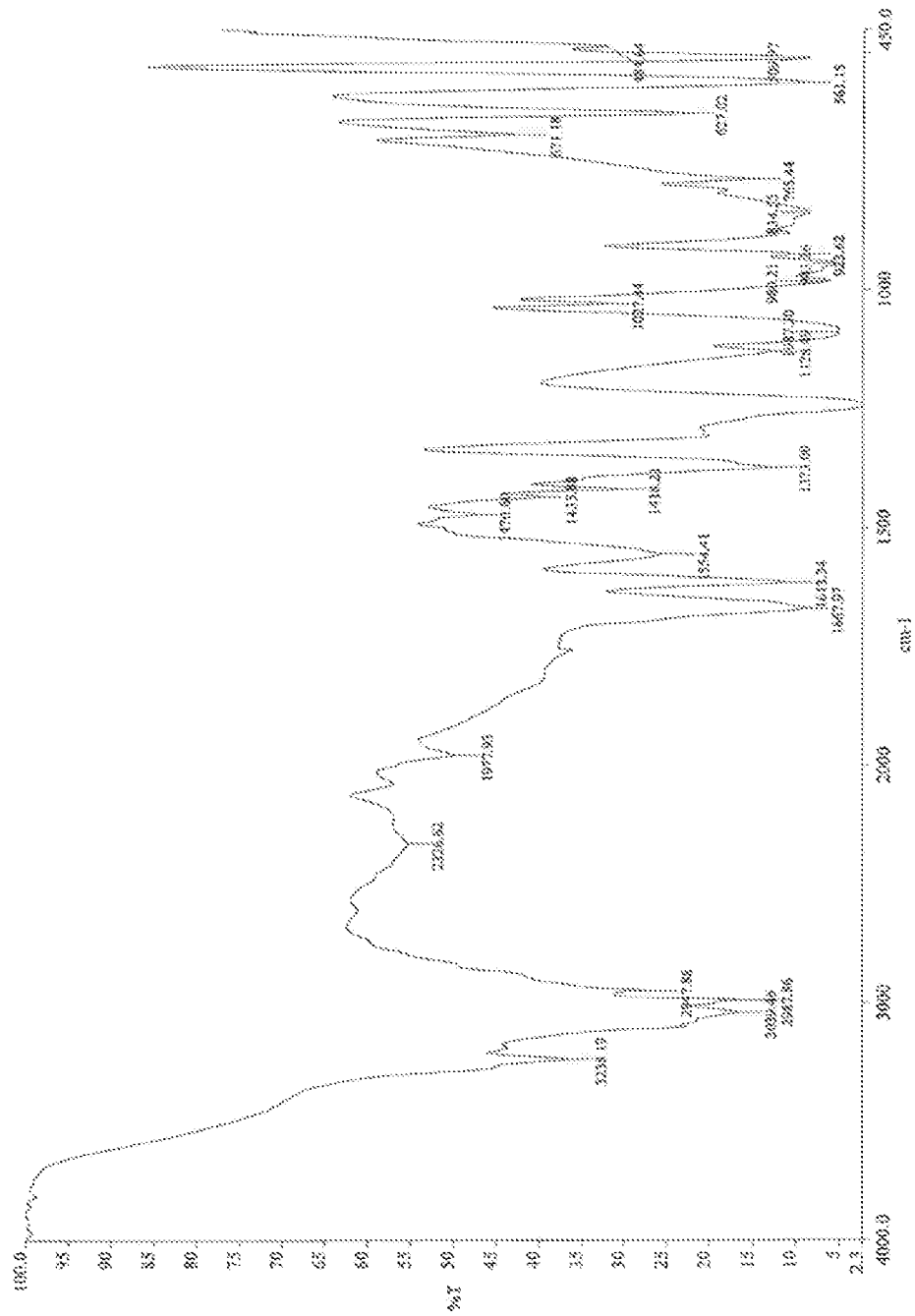
FIG. 3 illustrates the Fourier transform infrared spectrum of the crystals obtained in example 1.

The infrared spectrum of the solid according to example 1 (FIG. 3) did not present the same peaks.

Example 5: Preparation of the Crystalline Hydrated Form of Acrylamide/2-acrylamido-2-methylpropane Sulfonic Acid (Co)Polymer (75/25 Mole %)

To a 2000 mL beaker are added 549.5 g of deionized water, 520.5 g of 50% acrylamide solution, 97.6 g of 50% sodium hydroxide, 16.2 g of urea and 316.2 g crystals of 2-acrylamido-2-methylpropane sulfonic acid obtained in example 2.

The resulting solution is cooled between 5 and 10° C. and transferred to an adiabatic polymerization reactor, then nitrogen is bubbled for 30 minutes to remove all traces of dissolved oxygen.

The following are then added to the reactor:
- 0.45 g of 2,2'-azobisisobutyronitrile,
- 1.5 mL of a solution at 2.5 g/L of 2,2'-azobis[2-(2-imidazolin-2-yl)propane] dihydrochloride,
- 1.5 mL of a solution at 1 g/L of sodium hypophosphite,
- 1.5 mL of a solution at 1 g/L of tert-butyl hydroperoxide,
- 1.5 mL of a solution at 1 g/L of ammonium iron (II) sulfate hexahydrate (Mohr's salt).

After a few minutes, the nitrogen inlet is shut and the reactor is closed. The polymerization reaction occurs for 2 to 5 hours until a temperature peak is reached. The rubbery gel obtained is chopped and dried to obtain a coarse powder itself milled and sieved to obtain the polymer in powder form.

Example 6: Preparation of the Non-Crystalline Hydrated Form of the Acrylamide/2-acrylamido-2-methylpropane Sulfonic Acid (Co)Polymer (75/25 Mole %)

The polymers are prepared as in example 5, replacing the crystalline hydrated form of 2-acrylamido-2-methylpropane sulfonic acid (example 2) with 2-acrylamido-2-methylpropane sulfonic acid that is not the crystalline hydrated form synthesized in example 1.

Example 7: Measurement of the Filter Ratio for Polymer Solutions

Filtration tests were conducted on 3 polymers prepared from the non-crystalline form of 2-acrylamido-2-methylpropane sulfonic acid P'1, P'2 and P'3 with respective increasing molecular weights 6.5, 9 and 11.5 million Da, prepared as described in example 6, and on 4 polymers prepared from the crystalline form of 2-acrylamido-2-methylpropane sulfonic acid P1, P2, P3 and P4 with respective increasing molecular weights 6.5, 9, 11 and 13 million Da, prepared as described in example 5. The molecular weight grade 13 million Da is not accessible when the non-crystalline form of 2-acrylamido-2-methylpropane sulfonic acid is used.

Figure 5:
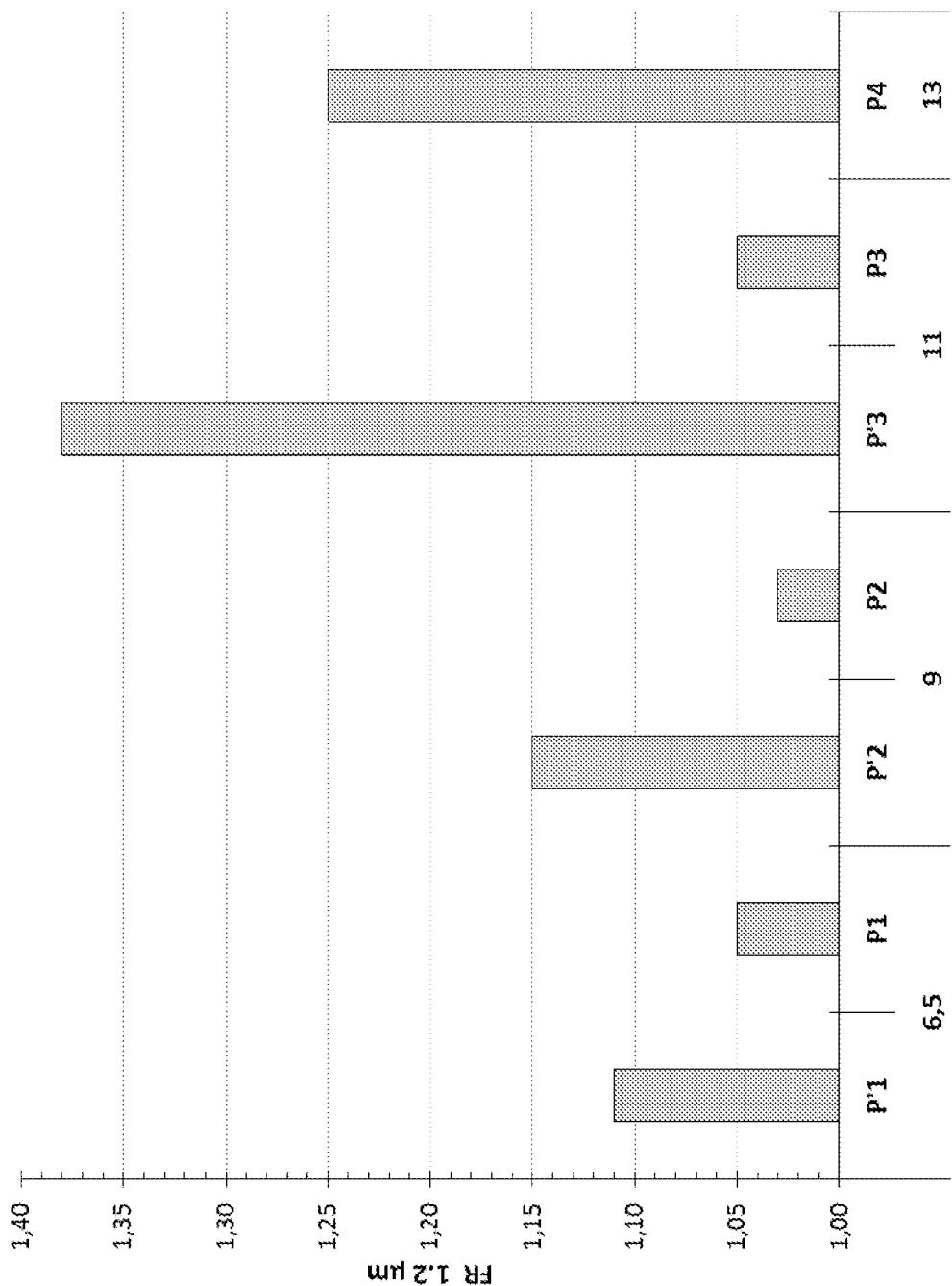
FIG. 5 illustrates the filter ratio as a function of the form of ATBS and the molecular weight of (co)polymers.

The polymer solutions were prepared at an active concentration of 1,000 ppm in a brine containing water, 30,000 ppm of NaCl and 3,000 ppm of $CaCl_2.2H_2O$. The filter ratio (FR) was measured in filters having a pore size of 1.2 μm representative of deposits with low permeability. These results are shown in FIG. 5.

TABLE 1

Polymers tested for the filter ratio

| | Form of ATBS used | Molecular weight (in million Da) | Filter ratio |
|---|---|---|---|
| P1 | Crystalline | 6.5 | 1.05 |
| P2 | Crystalline | 9 | 1.03 |
| P3 | Crystalline | 11 | 1.05 |
| P4 | Crystalline | 13 | 1.25 |
| P'1 | Non-crystalline | 6.5 | 1.11 |
| P'2 | Non-crystalline | 9 | 1.15 |
| P'3 | Non-crystalline | 11.5 | 1.38 |

We can observe that at equivalent molecular weight, the polymers prepared from the hydrated crystalline form of 2-acrylamido-2-methylpropane sulfonic acid (P1-P3) always have a FR lower than that of the polymers prepared from the non-crystalline form of 2-acrylamido-2-methylpropane sulfonic acid (P'1-P'3). This difference becomes bigger and bigger when the molecular weight of the polymer increases. The polymer made from the crystalline form of 2-acrylamido-2-methylpropane sulfonic acid with molecular weight 13 million Da (P4) even has a lower FR than the polymer prepared from the non-crystalline form of 2-acrylamido-2-methylpropane sulfonic acid with lower molecular weight (11.5 million Da, P'3).

Figure 6:
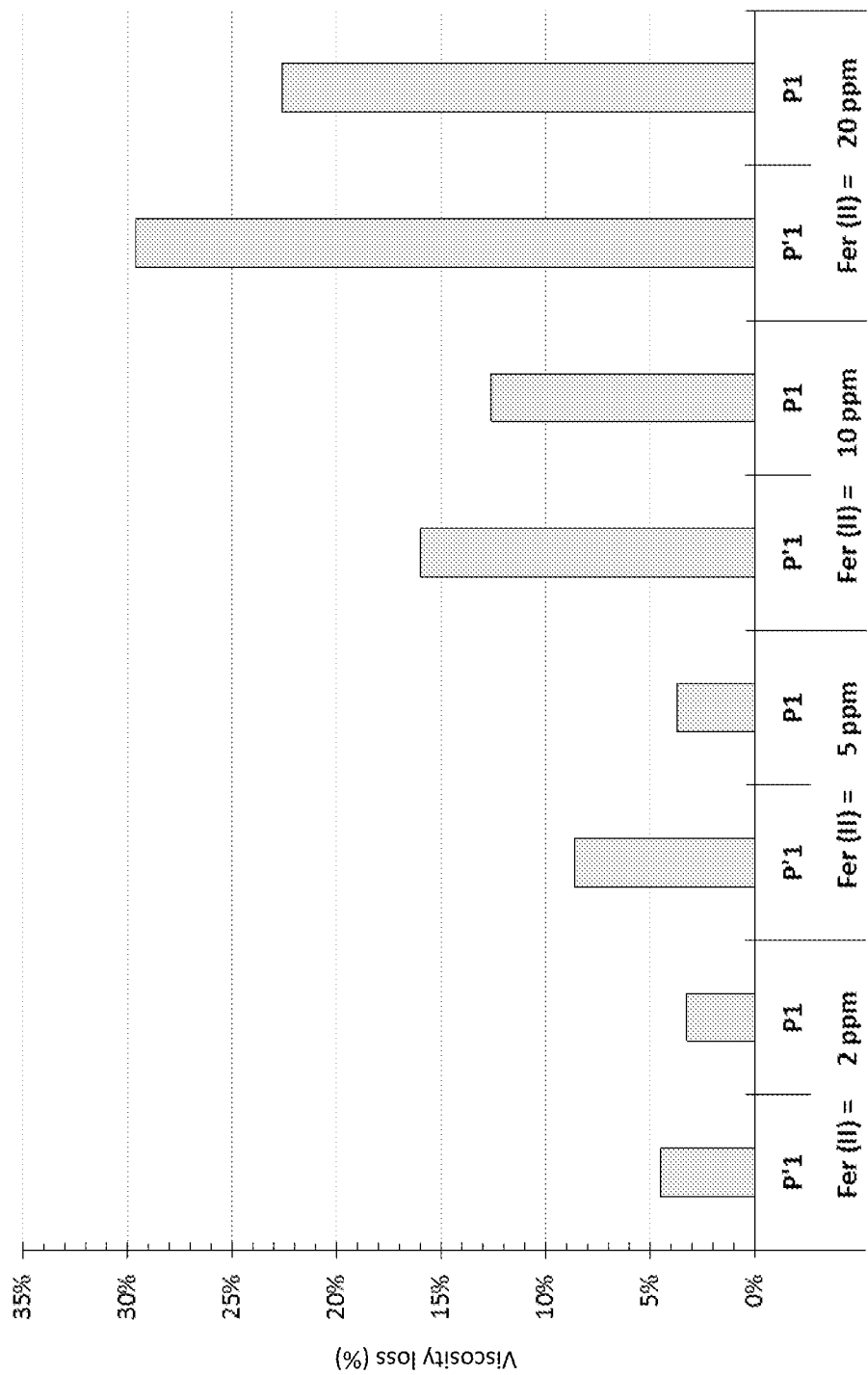
FIG. 6 illustrates the viscosity loss as a function of the form of ATBS and the iron content of (co)polymers.

Example 8: Measurement of the Resistance to Chemical Degradation of Solutions of Polymers with Equivalent Molecular Weights Resistance tests for chemical degradation of polymers P3 and P'3 were conducted in aerobic conditions in the presence of different iron(II) concentrations (2, 5, 10 and 20 ppm) in a brine composed of water, 37,000 ppm of NaCl, 5,000 ppm of $Na_2SO_4$ and 200 ppm of $NaHCO_3$. These tests have been conducted on a polymer prepared from the non-crystalline form of 2-acrylamido-2-methylpropane sulfonic acid (P'3) and on a polymer made from the crystalline form of 2-acrylamido-2-methylpropane sulfonic acid (P3). The two polymers have the same chemical composition. The results after 24 h of contact of the polymer solution with the contaminant are shown in FIG. 6.

We can observe that for each iron(II) concentration, polymer P3 loses less viscosity than the equivalent polymer P'3.

Figure 7:
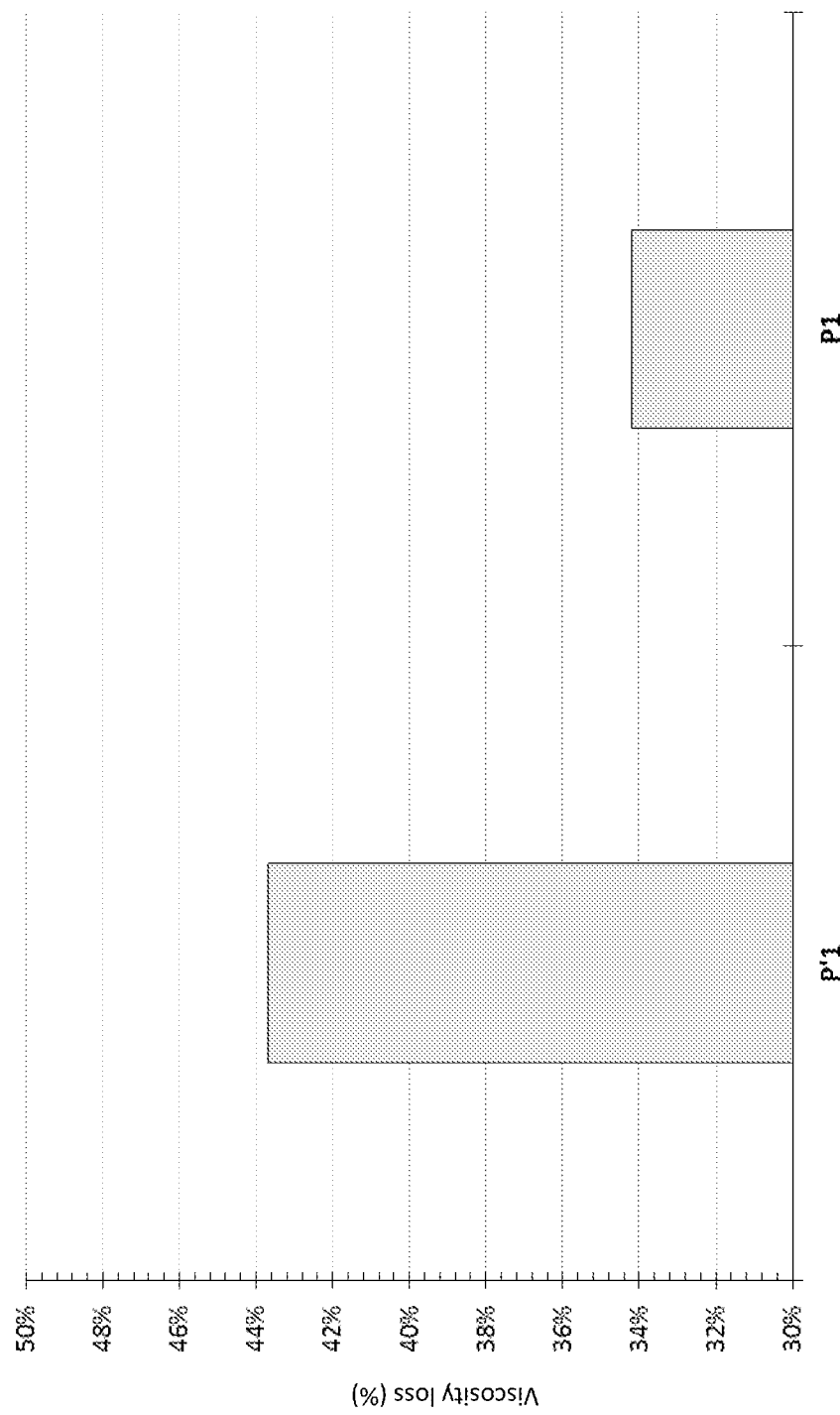
FIG. 7 illustrates the viscosity loss as a function of the form of ATBS and aging at 90° C. of (co)polymers.

Example 9: Measurement of the Resistance to Thermal Degradation of Solutions of Polymers with Equivalent Molecular Weights Tests of resistance to thermal degradation for polymers P3 and P'3 were conducted in anaerobic conditions at an active concentration of 2,000 ppm in a brine composed of 30,000 ppm of NaCl and 3,000 ppm of $CaCl_2 \cdot 2H_2O$. These tests have been conducted on a polymer prepared from the non-crystalline form of 2-acrylamido-2-methylpropane sulfonic acid (P'3) and on a polymer made from the crystalline form of 2-acrylamido-2-methylpropane sulfonic acid (P3). The two polymers have the same chemical composition. The polymer solutions were observed for 6 months at 90° C. The results for viscosity loss are shown in FIG. 7. We can observe that polymer P3 loses less viscosity than the equivalent polymer P'3.

Example 10: Preparation of Homopolymers from the Hydrated Crystalline Form of 2-acrylamido-2-methylpropane Sulfonic Acid To a 2000 mL beaker are added 390.5 g of deionized water, 262 g of 50% sodium hydroxide and 847.5 g crystals of 2-acrylamido-2-methylpropane sulfonic acid obtained in example 2.

The resulting solution is cooled between 5 and 10° C. and transferred to an adiabatic polymerization reactor, then nitrogen is bubbled for 30 minutes to remove all traces of dissolved oxygen.

The following are then added to the reactor:
0.45 g of 2,2'-azobisisobutyronitrile,
1.5 mL of a solution at 2.5 g/L of 2,2'-azobis[2-(2-imidazolin-2-yl)propane] dihydrochloride,
1.5 mL of a solution at 1 g/L of sodium hypophosphite,
1.5 mL of a solution at 1 g/L of tert-butyl hydroperoxide,
1.5 mL of a solution at 1 g/L of ammonium iron (II) sulfate hexahydrate (Mohr's salt).

After a few minutes, the nitrogen inlet is shut and the reactor is closed. The polymerization reaction occurs for 2 to 5 hours until a temperature peak is reached. The rubbery gel obtained is chopped and dried to obtain a coarse powder itself milled and sieved to obtain the polymer in powder form.

Example 11: Preparation of Homopolymers from the Non-Crystalline Hydrated Form of 2-acrylamido-2-methylpropane Sulfonic Acid The polymers are prepared as in example 10, replacing the crystalline hydrated form of 2-acrylamido-2-methylpropane sulfonic acid (example 2) with 2-acrylamido-2-methylpropane sulfonic acid that is not the crystalline hydrated form synthesized in example 1.

Example 12: Measurement of the Filter Ratio for Polymer Solutions

Filtration tests were conducted on 2 polymers prepared from the non-crystalline form of 2-acrylamido-2-methylpropane sulfonic acid P'5, P'6 with respective increasing molecular weights 3.1 and 5.3 million Da, prepared as described in example 11, and on 3 polymers prepared from the crystalline form of 2-acrylamido-2-methylpropane sulfonic acid P5, P6 and P7 with respective increasing molecular weights 3.1, 5.3 and 15 million Da, prepared as described in example 10. The molecular weight grade 15 million Da is not accessible when the non-crystalline form of 2-acrylamido-2-methylpropane sulfonic acid is used.

Figure 8:
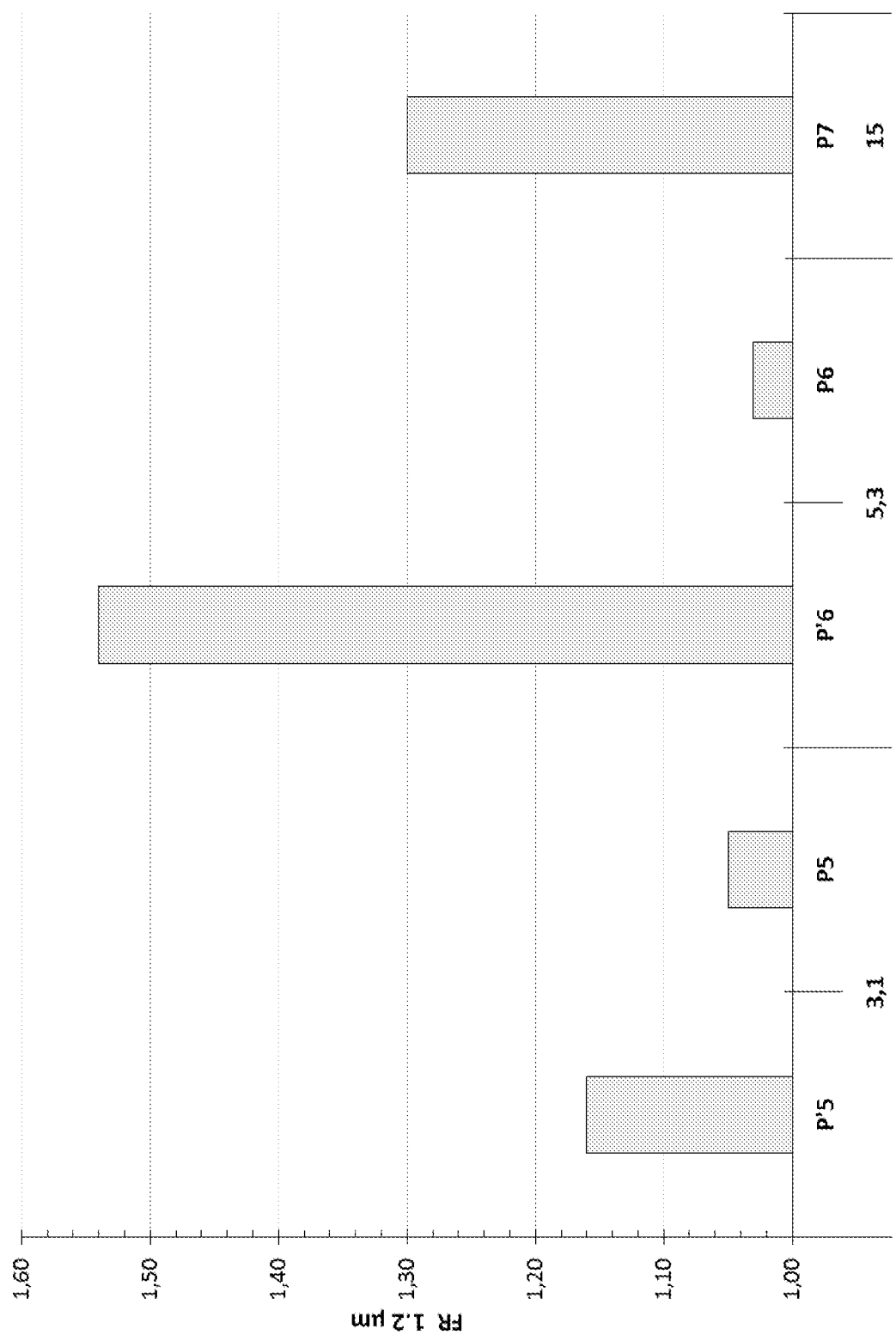
FIG. 8 illustrates the filter ratio as a function of the form of ATBS and the molecular weight of homopolymers.

The polymer solutions were prepared at an active concentration of 1,000 ppm in a brine containing water, 30,000 ppm of NaCl and 3,000 ppm of $CaCl_2 \cdot 2H_2O$. The filter ratio (FR) was measured in filters having a pore size of 1.2 μm representative of deposits with low permeability. These results are shown in FIG. 8.

TABLE 2

| Polymers tested for the filter ratio | | | |
| --- | --- | --- | --- |
| | Form of ATBS used | Molecular weight (in million Da) | Filter ratio |
| P5 | Crystalline | 3.1 | 1.05 |
| P6 | Crystalline | 5.3 | 1.03 |
| P7 | Crystalline | 15 | 1.30 |
| P'5 | Non-crystalline | 3.1 | 1.16 |
| P'6 | Non-crystalline | 5.3 | 1.54 |

We can observe that at equivalent molecular weight, the polymers made from the hydrated crystalline form of 2-acrylamido-2-methylpropane sulfonic acid (P5-P6) always have a FR lower than that of the polymers made from the non-crystalline form of 2-acrylamido-2-methylpropane sulfonic acid (P'5-P'6). This difference becomes bigger and bigger when the molecular weight of the polymer increases. The polymer prepared from the crystalline form of 2-acrylamido-2-methylpropane sulfonic acid with molecular weight 15 million Da (P7) even has a lower FR than the polymer prepared from the non-crystalline form of 2-acrylamido-2-methylpropane sulfonic acid with lower molecular weight (5.3 million Da, P'6).

Example 13: Measurement of the Resistance to Chemical Degradation of Solutions of Polymers P6 and P'6

Figure 9:
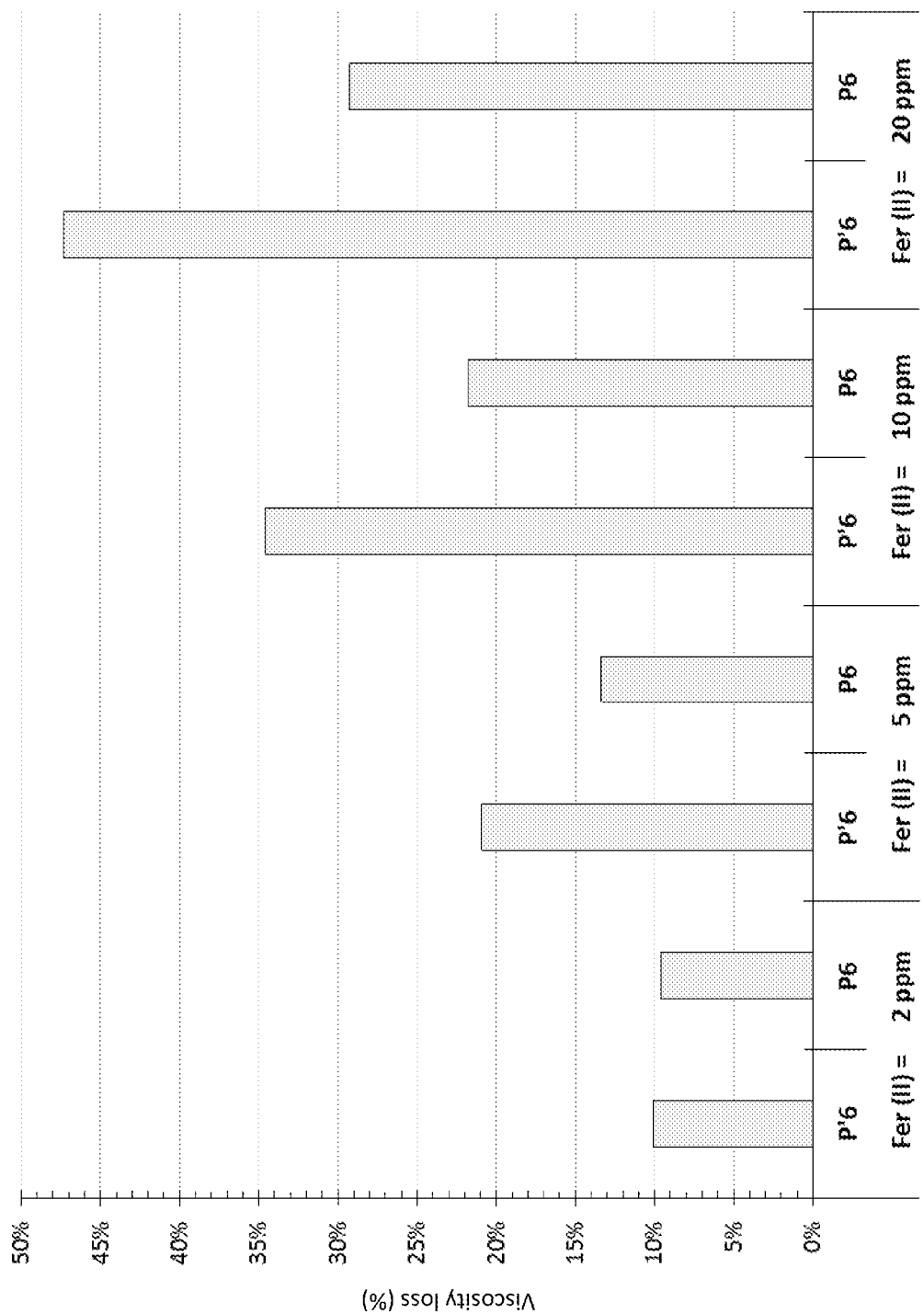
FIG. 9 illustrates the viscosity loss as a function of the form of ATBS and the iron content of homopolymers.

Resistance tests for chemical degradation of polymers P6 and P'6 with molecular weight 5.3 million Da were conducted in aerobic conditions in the presence of different iron(II) concentrations (2, 5, 10 and 20 ppm) in a brine composed of water, 37,000 ppm of NaCl, 5,000 ppm of $Na_2SO_4$ and 200 ppm of $NaHCO_3$. These tests have been conducted on a polymer prepared from the non-crystalline form of 2-acrylamido-2-methylpropane sulfonic acid (P'6) and on a polymer made from the crystalline form of 2-acrylamido-2-methylpropane sulfonic acid (P6). The two polymers have the same chemical composition. The results after 24 h of contact of the polymer solution with the contaminant are shown in FIG. 9.

We can observe that for each iron(II) concentration, polymer P6 loses less viscosity than the equivalent polymer P'6.

Example 14: Preparation of the Crystalline Hydrated Form of Acrylamide/2-acrylamido-2-methylpropane Sulfonic Acid (Co)Polymer (75/25 Mole %), Post-Hydrolyzed, P8

To a 2000 mL beaker are added 761.9 g of deionized water, 574.2 g of 50% acrylamide solution, 35.9 g of 50% sodium hydroxide, 11.7 g of urea and 116.3 g crystals of 2-acrylamido-2-methylpropane sulfonic acid obtained in example 2.

The resulting solution is cooled between 0 and 5° C. and transferred to an adiabatic polymerization reactor, then nitrogen is bubbled for 30 minutes to remove all traces of dissolved oxygen.

The following are then added to the reactor:

0.45 g of 2,2'-azobisisobutyronitrile, 1.5 mL of a 5 g/L solution of 2,2'-azobis[2-(2-imidazolin-2-yl)propane] dihydrochloride, 1.5 mL of a solution at 1 g/L of sodium hypophosphite, 2.25 mL of a solution at 1 g/L of tert-butyl hydroperoxide, 3.0 mL of a solution at 1 g/L of ammonium iron (II) sulfate hexahydrate (Mohr's salt).

After a few minutes, the nitrogen inlet is shut and the reactor is closed. The polymerization reaction occurs for 2 to 5 hours until a temperature peak is reached. The rubbery gel obtained is chopped into particles with a size inclusively between 1 and 6 mm.

500.0 g of previously chopped gel is then mixed with 18.0 g of 50% sodium hydroxide, the mixture is taken and held at a temperature of 90° C. for a duration of 90 minutes.

The gel is then dried and milled to obtain the polymer in powder form.

Example 15: Preparation of the Non-Crystalline Hydrated Form of Acrylamide/2-acrylamido-2-methylpropane Sulfonic Acid (Co)Polymer (75/25 Mole %), Post-Hydrolyzed, P'8

The copolymer is prepared as in example 14, replacing the crystalline hydrated form of 2-acrylamido-2-methylpropane sulfonic acid (example 2) with 2-acrylamido-2-methylpropane sulfonic acid that is not the crystalline hydrated form obtained in example 1.

Example 16: Measurement of the Filter Ratio for Polymer Solutions

Filtration tests were conducted on a polymer prepared from the non-crystalline form of 2-acrylamido-2-methylpropane sulfonic acid P'8 with molecular weight of 22 million Da, prepared as described in example 15, and on a polymer prepared from the hydrated crystalline form of 2-acrylamido-2-methylpropane sulfonic acid P8 with molecular weight of 26 million Da, prepared as described in example 14.

Figure 10:
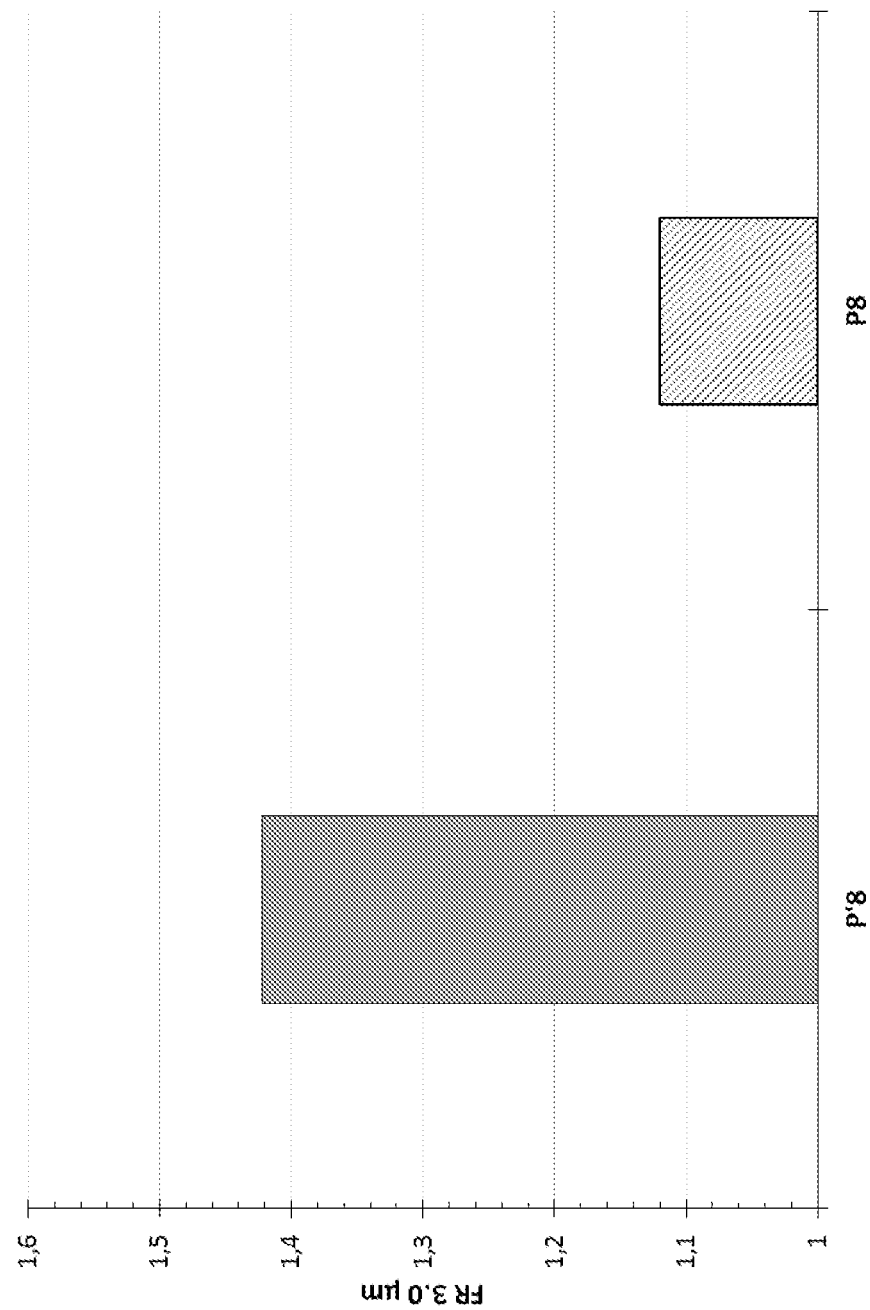
FIG. 10 illustrates the filter ratio as a function of the form of ATBS and the molecular weight of post-hydrolyzed (co)polymers.

The polymer solutions were prepared at an active concentration of 1,000 ppm in a brine containing water, 30,000 ppm of NaCl and 3,000 ppm of $CaCl_2 \cdot 2H_2O$. The filter ratio (FR) was measured in filters having a pore size of 3 μm representative of deposits with low permeability. These results are shown in FIG. 10.

TABLE 3

Polymers tested for the filter ratio

|  | Form of ATBS used | Molecular weight (in million Da) | Filter ratio |
|---|---|---|---|
| P8 | Hydrated crystalline | 26 | 1.07 |
| P'8 | Non-crystalline | 22 | 1.10 |

We can observe that, in spite of a higher molecular weight, the (co)polymer prepared from the hydrated crystalline form of 2-acrylamido-2-methylpropane sulfonic acid (P8) presents a FR equivalent to that of the (co)polymer made from the non-crystalline form of 2-acrylamido-2-methylpropane sulfonic acid (P'8).

What is claimed is:

1. A process for enhanced oil recovery comprising the following steps:
    a. preparing an injection fluid comprising at least one water-soluble (co)polymer prepared at least from 2-acrylamido-2-methylpropane sulfonic acid (ATBS) or from at least one of its salts, with water or with brine, wherein the 2-acrylamido-2-methylpropane sulfonic acid is a hydrated crystalline form of 2-acrylamido-2-methylpropane sulfonic acid having a 2-theta powder X-ray diffraction diagram comprising peaks at 10.58°, 11.2°, 12.65°, 13.66°, 16.28°, 18.45°, 20°, 20.4°, 22.5°, 25.5°, 25.88°, 26.47°, 28.52°, 30.28°, 30.8°, 34.09°, 38.19°, 40.69°, 41.82°, 43.74°, and 46.04° degrees;
    b. injecting injection fluid into an underground formation;
    c. flushing of the underground formation using the fluid injected; and
    d. recovering an aqueous and hydrocarbon mixture.

2. The process according to claim 1, wherein the injection fluid comprises between 10 ppm and 15,000 ppm of water-soluble (co)polymer.

3. The process according to claim 2, wherein the water-soluble (co)polymer is prepared at least from 2-acrylamido-2-methylpropane sulfonic acid of which 50% to 100% is in the hydrated crystalline form.

4. The process according to claim 2, wherein the water-soluble (co)polymer is a (co)polymer obtained at least from 2-acrylamido-2-methylpropane sulfonic acid of which 50% to 100% is in the hydrated crystalline form and of at least one nonionic monomer and/or at least one anionic monomer and/or at least one cationic monomer and/or a zwitterionic monomer.

5. The process according to claim 4, wherein the nonionic monomer is chosen from acrylamide, methacrylamide, N-isopropylacrylamide, N,N-dimethylacrylamide, N,N-diethylacrylamide, N-methylolacrylamide, N-vinylformamide, N-vinyl acetamide, N-vinylpyridine, N-vinylpyrrolidone, N-vinyl imidazole, N-vinyl succinimide, acryloyl morpholine (ACMO), acryloyl chloride, glycidyl methacrylate, glyceryl methacrylate, diacetone acrylamide and isoprenol.

6. The process according to claim 4, wherein the anionic monomer is chosen from acrylic acid, methacrylic acid, itaconic acid, crotonic acid, maleic acid, fumaric acid, acrylamido undecanoic acid, 3-acrylamido 3-methylbutanoic acid, maleic anhydride, vinylsulfonic acid, vinylphosphonic acid, allylsulfonic acid, methallylsulfonic acid, 2-methylidenepropane-1,3-disulfonic acid, 2-sulfoethylmethacrylate, sulfopropylmethacrylate, sulfopropylacrylate, allylphosphonic acid, styrene sulfonic acid, 2-acrylamido-2-methyl propane disulfonic acid; and water-soluble salts of these monomers like their alkali metal, alkaline earth metal, or ammonium salts.

7. The process according to claim 2, wherein the water-soluble (co)polymer is a (co)polymer obtained at least from 2-acrylamido-2-methylpropane sulfonic acid of which 50% to 100% is in the hydrated crystalline form and of at least one nonionic monomer and/or at least one anionic monomer, and wherein:
    the nonionic monomer is chosen from acrylamide, methacrylamide, N-isopropylacrylamide, N,N-dimethylacrylamide, N,N-diethylacrylamide, N-methylolacrylamide, N-vinylformamide, N-vinyl acetamide, N-vinylpyridine, N-vinylpyrrolidone, N-vinyl imidazole, N-vinyl succinimide, acryloyl morpholine (ACMO), acryloyl chloride, glycidyl methacrylate, glyceryl methacrylate, diacetone acrylamide and isoprenol; and the anionic monomer is chosen from acrylic acid, methacrylic acid, itaconic acid, crotonic acid, maleic acid, fumaric acid, acrylamido undecanoic acid, 3-acrylamido 3-methylbutanoic acid, maleic anhydride, vinylsulfonic acid, vinylphosphonic acid, allylsulfonic acid, methallylsulfonic acid, 2-methylidenepropane-1,3-disulfonic acid, 2-sulfoethylmethacrylate, sulfopropylmethacrylate, sulfopropylacrylate, allylphosphonic acid, styrene sulfonic acid, 2-acrylamido-2-methyl propane disulfonic acid; and water-soluble salts of these monomers like their alkali metal, alkaline earth metal, or ammonium salts.

8. The process according to claim 7, wherein the injection fluid comprises between 50 ppm and 10,000 ppm of (co)polymer.

9. The process according to claim 8, wherein the injection fluid comprises between 100 and 5,000 ppm of (co)polymer.

10. The process according to claim 7, wherein the (co)polymer is obtained at least from the 2-acrylamido-2-methylpropane sulfonic acid of which 50% to 100% is in the hydrated crystalline form and the at least one nonionic monomer.

11. The process according to claim 7, wherein the (co)polymer is obtained at least from the 2-acrylamido-2-methylpropane sulfonic acid of which 50% to 100% is in the hydrated crystalline form and the at least one anionic monomer.

12. The process according to claim 1, wherein the water-soluble (co)polymer is prepared at least from 2-acrylamido-2-methylpropane sulfonic acid of which 50% to 100% is in the hydrated crystalline form.

13. The process according to claim 1, wherein the water-soluble (co)polymer is a (co)polymer obtained at least from 2-acrylamido-2-methylpropane sulfonic acid of which 50% to 100% is in the hydrated crystalline form and of at least one nonionic monomer and/or at least one anionic monomer and/or at least one cationic monomer and/or a zwitterionic monomer.

14. The process according to claim 13, wherein the nonionic monomer is chosen from acrylamide, methacrylamide, N-isopropylacrylamide, N,N-dimethylacrylamide, N,N-diethylacrylamide, N-methylolacrylamide, N-vinylformamide, N-vinyl acetamide, N-vinylpyridine, N-vinylpyrrolidone, N-vinyl imidazole, N-vinyl succinimide, acryloyl morpholine (ACMO), acryloyl chloride, glycidyl methacrylate, glyceryl methacrylate, diacetone acrylamide and isoprenol.

15. The process according to claim 13, wherein the anionic monomer is chosen from acrylic acid, methacrylic acid, itaconic acid, crotonic acid, maleic acid, fumaric acid, acrylamido undecanoic acid, 3-acrylamido 3-methylbutanoic acid, maleic anhydride, vinylsulfonic acid, vinylphosphonic acid, allylsulfonic acid, methallylsulfonic acid, 2-methylidenepropane-1,3-disulfonic acid, 2-sulfoethylmethacrylate, sulfopropylmethacrylate, sulfopropylacrylate, allylphosphonic acid, styrene sulfonic acid, 2-acrylamido-2-methyl propane disulfonic acid; and water-soluble salts of these monomers like their alkali metal, alkaline earth metal, or ammonium salts.

16. The process according to claim 1, wherein the injection fluid comprises between 50 ppm and 10,000 ppm of (co)polymer.

17. The process according to claim 16, wherein the injection fluid comprises between 100 and 5,000 ppm of (co)polymer.

18. The process according to claim 1, wherein the water-soluble (co)polymer is a homopolymer prepared from the hydrated crystalline form of 2-acrylamido-2-methylpropane sulfonic acid.

19. The process according to claim 18, wherein the injection fluid comprises between 50 ppm and 10,000 ppm of (co)polymer.

20. The process according to claim 19, wherein the injection fluid comprises between 100 and 5,000 ppm of (co)polymer.

* * * * *